US006814982B2

(12) United States Patent
Poncin et al.

(10) Patent No.: US 6,814,982 B2
(45) Date of Patent: Nov. 9, 2004

(54) SUSPENSION OF AN EPI-HNE PROTEIN, PROCESS OF PREPARATION THEREOF, DRY POWDER AEROSOL DERIVED THEREFROM, PHARMACEUTICAL COMPOSITIONS CONTAINING SAID SUSPENSION OR AEROSOL, AND THEIR USES

(75) Inventors: Alain Poncin, Boncelles (BE); François Saudubray, Preverenges (CH); Anne Bokman, Martigny (CH)

(73) Assignee: Debiopharm S.A., Lausanne (CH)

( * ) Notice: Subject to any disclaimer, the term of this patent is extended or adjusted under 35 U.S.C. 154(b) by 0 days.

(21) Appl. No.: 10/417,854

(22) Filed: Apr. 17, 2003

(65) Prior Publication Data

US 2004/0013659 A1 Jan. 22, 2004

Related U.S. Application Data

(63) Continuation of application No. PCT/EP01/12983, filed on Oct. 26, 2001.

(30) Foreign Application Priority Data

Oct. 31, 2000 (EP) .............................................. 00403035
Jun. 28, 2001 (EP) .............................................. 01401731

(51) Int. Cl.[7] .............................. A61K 9/00; A61K 9/14; A61K 38/00; A61K 38/16; A61K 38/17
(52) U.S. Cl. ........................ 424/499; 424/400; 424/489

(58) Field of Search .................................. 424/400, 489, 424/499

(56) References Cited

FOREIGN PATENT DOCUMENTS

| EP | 00203049.2 | 9/2000 |
|---|---|---|
| WO | WO 92/15605 | 2/1992 |
| WO | WO 96/20278 | 12/1995 |

OTHER PUBLICATIONS

Delacourt, C. et al. "Protection Against Acute Lung Injury by Intravenous or Intratrachel Pretreatment with EPI–hNE–4, a New Potent Neutrophil Elastase Inhibitor". Am. J. Respir. Cell Mol. Biol. 26 (2002): 290–297.*
Grimbert, D. et al. "Characteristics of EPI–hNE4 Aerosol: A New Elastase Inhibitor for Treatment of Cystic Fibrosis". J. of Aerosol Medicine. 16 (2003): 121–129.*

* cited by examiner

Primary Examiner—Thurman K. Page
Assistant Examiner—Simon J. Oh
(74) Attorney, Agent, or Firm—Sturm & Fix LLP

(57) ABSTRACT

The present invention concerns a suspension of crystallized particles of an EPI-hNE protein, methods for preparing said suspension, a dry powder aerosol derived from said suspension, an inhalable pharmaceutical formulation comprising said suspension or said dry powder aerosol, and the use of said inhalable pharmaceutical formulation in the treatment of various pathological conditions.

22 Claims, 3 Drawing Sheets

20278 to Ley et al. describes a number of genetically engineered novel proteins which inhibit human neutrophil elastase (hNE). As indicated in the above-cited patent application, human neutrophil elastase (also known as human leukocyte elastase) is one of the major neutral proteases of the azurophil granules of polymorphonuclear leukocytes. This enzyme is involved in the elimination of pathogens, and in connective tissue restructuring.

SUSPENSION OF AN EPI-HNE PROTEIN, PROCESS OF PREPARATION THEREOF, DRY POWDER AEROSOL DERIVED THEREFROM, PHARMACEUTICAL COMPOSITIONS CONTAINING SAID SUSPENSION OR AEROSOL, AND THEIR USES

This is a cont. of PCT No. EP01/12983 filed Oct. 26, 2001.

The present invention concerns a suspension of crystallized particles of an EPI-hNE protein, methods for preparing said suspension, a dry powder aerosol derived from said suspension, an inhalable pharmaceutical formulation comprising said suspension or said dry powder aerosol, and the use of said inhalable pharmaceutical formulation in the treatment of various pathological conditions.

International Patent Application WO 96/20278 to Ley et al. describes a number of genetically engineered novel proteins which inhibit human neutrophil elastase (hNE). As indicated in the above-cited patent application, human neutrophil elastase (also known as human leukocyte elastase) is one of the major neutral proteases of the azurophil granules of polymorphonuclear leukocytes. This enzyme is involved in the elimination of pathogens, and in connective tissue restructuring.

The principal systemic inhibitor of hNE is the α-1-protease inhibitor, formerly known as α1 antitrypsin. In a certain number of pathological situations (hereditary disorders, chronic bronchitis, emphysema, cystic fibrosis), this inhibitor is either not present in sufficient amounts in the bloodstream or is inactivated, leading to uncontrolled elastolytic activity of hNE, which causes extensive destruction of lung tissue.

WO 96/20278 thus proposes novel proteins which are stable, non-toxic, highly efficacious inhibitors of hNE. These inhibitors form part of a group of inhibitors derived from a Kunitz-type inhibitory domain found in basic pancreatic trypsin inhibitor (BPTI) or a protein of human origin, namely the light chain of human Inter-α-trypsin inhibitor (ITI). They are, inter alia, EPI-hNE-1, EPI-hNE-2, EPI-hNE-3 and EPI-hNE-4. The inhibitors of WO 96/20278 are produced by biotechnological methods and contain modified DNA sequences, with respect to the biological Kunitz domains, which render them highly potent. One of these inhibitors, EPI-hNE-4, is of particular interest.

WO 96/20278 describes preparation of *Pichia pastoris* production systems for hNE inhibitors EPI-hNE1, EPI-hNE-2, EPI-hNE-3 and EPI-hNE-4, protein production and purification (see in particular Examples 10–15).

Yeast *Pichia pastoris* mutant strain GS115 containing a non functional histidinol dehydrogenase gene (his4) was transformed by expression plasmids comprising a sequence encoding the *S. cerevisiae* mating factor alpha prepro peptide fused directly to the amino terminus of the desired hNE inhibitor, under control of the upstream inducible *P. pastoris* aox1 gene promoter and the downstream aox1 transcription termination and polyadenylation sequences. The expression plasmids were linearized by SacI digestion and the linear DNA was incorporated by homologous recombination into the genome of the *P. pastoris* strain GS115 by spheroplast transformation, selection for growth in the absence of added histidine and screening for methanol utilization phenotype, secretion levels and gene dose (estimated by Southern Blot). Strains estimated to have about four copies of the expression plasmid integrated as a tandem array into the aox1 gene locus were thus selected.

Cultures of selected strains were first grown in batch mode with glycerol as the carbon source, then, following exhaustion of glycerol, grown in glycerol-limited feed mode to further increase cell mass and derepress the aox1 promoter and finally in methanol-limited feed mode. During the latter phase the aox1 promoter is fully active and the protein is secreted into the culture medium.

The EPI-hNE protein is then purified. The specific purification procedure varies with the specific properties of each protein. Briefly, the culture medium is centrifuged, the supernatant is subjected to microfiltration and subsequently to ultrafiltration, optionally to diafiltration, and then the protein is recovered by ammonium sulfate precipitation and ion exchange chromatography.

European Patent Application No. 00203049.2 and international patent application PCT/FR 01/02699 claiming priority thereof, filed by the applicant company, describe an improved process for the purification of an EPI-HNE protein of pharmaceutical quality, from the culture medium of a host strain for the expression of said proteins, comprising the steps of:

(a) passing a derived part of the culture medium over an expanded, bed of cationic exchange adsorbent in order to recover an eluate, (b) conducting separation of proteins, according to their hydrophobicity, on the resulting eluate, (c) passing the resulting eluate over a cationic exchange column, (d) optionally filtering the resulting medium under sterile conditions, and (e) optionally lyophilising the resulting filtrate in order to recover an EPI-HNE protein.

The solution obtained at the end of step (d) or a freeze dried powder obtained therefrom can be used to prepare the suspension according to the present invention, said suspension being capable of being incorporated in an inhalable pharmaceutical formulation according to the invention.

The applicant company, having perfected a purification method of EPI-hNE proteins, particularly EPI-hNE-4, has subsequently devoted a great deal of research and effort to the development of pharmaceutical compositions containing the purified EPI-hNE proteins.

In fact, the Applicant Company has concentrated on the development of a buccal inhalable pharmaceutical composition containing a solution of Epi-hNE-4. However, in the course of product development, it was found that the solution of EPI-hNE-4, once in the nebulizer, was unstable and tended to precipitate, rendering the solution turbid.

It was first thought that the precipitated form of the protein would be therapeutically inactive. However, in a surprising and unexpected manner, it was found that the precipitated form was a crystallized form of EPI-HNE4 and that this crystallization did not adversely affect the activity of the protein. The term "crystallized form of EPI-hNE4" here means an insoluble form of this protein, having a rod-like structure and a particle size mainly below 10 μm.

The applicant company thus turned its efforts towards developing a suspension of the EPI-hNE proteins in which the protein would be in crystalline form, said suspension being capable of being incorporated into a pharmaceutical composition, in particular an inhalable pharmaceutical formulation.

It was surprisingly found that it was possible to prepare a suspension which is stable at room temperature under certain specific conditions of concentration and pH, thereby allowing the preparation of pharmaceutical compositions incorporating said suspension which are stable at room temperature. This room temperature stability is of particular importance for ambulatory treatments.

The use of a suspension of EPI-hNE proteins, instead of a solution, constitutes a major advantage in the preparation of inhalable pharmaceutical compositions, insofar as it allows the development of a formulation which is more concentrated in active substance, thereby permitting administration of the drug in a shorter time frame.

This is an important factor in the administration of inhalable drugs since the time period of inhalation required can often be long, which is perceived as a major constraint and may hence lead to poor patient compliance.

Thus, the present invention concerns a suspension of an EPI-hNE protein, said suspension being characterized in that the EPI-hNE protein is present in the form of crystalline particles mostly having a particle size comprised between 1 and 6 µm, in particular between 3 and 6 µm, as determined by laser granulometry, the concentration of the suspension in the EPI-hNE protein being comprised between 1 and 80 mg/ml, preferably between 2 and 50 mg/ml, most preferably depending on the amount of the EPI-hNE protein required for the treated therapeutic condition, in an aqueous vehicle at a pH comprised between 3and 8, preferably 4 and 6, most preferably at a pH of 4.0 to 5.0.

The above suspension is stable as to its biological activity and particle size distribution for a period of at least two months at room temperature.

The aqueous vehicle is preferably a saline solution having an iso-osmotic pressure.

The saline solution may comprise sodium acetate and sodium chloride or sodium citrate.

The EPI-hNE protein is suitably selected from the group consisting of EPI-hNE-1, EPI-hNE-2, EPI-hNE-3, and EPI-hNE-4, preferably EPI-hNE-3 or EPI-HNE4. Most preferably it is EPI-hNE4.

The above suspension then preferably comprises at least 65% of the crystalline particles of EPI-HNE4 having a particle size between 3 and 6 µm, as determined by laser granulometry.

The inhaled mass of this suspension, determined on a Pari LC-star Nebuliser, is about 40 to 50%, which is a good value for an inhalable pharmaceutical formulation.

The MMAD (Median Mass Aerodynamic Diameter) of the nebulisate droplets containing EPI-HNE4 crystallized particles is about 2 µm, as determined by impactor granulometry. This MMAD value is well suited to ensure a high respirable fraction and an effective penetration into the lungs.

A dry powder can be derived from said suspension e.g. by submitting the latter to centrifugation, preferably after adjusting its pH to 3.5 to 4.5, separating the supernatant, gently vacuum-drying the pellet, then homogenizing so as to individualize the particles from the agglomerates. Under these conditions, spheroid-like particles which mostly have a particle size or diameter between 1 and 6 µm, as determined by direct microscopy, are obtained. The dry powder has a size distribution comparable to that of the suspension, when determined in solution by laser granulometry.

A dry powder can also be derived from a solution of EPI-hNE protein, or a freeze-dried powder of EPI-hNE protein.

The invention thus also relates to a dry powder which comprises spheroid-like particles of EPI-hNE-4 mostly having a particle size or diameter of between 1 and 6 µm, preferably at least 75% of the particles having a particle size or diameter between 1 and 3 µm, as determined by direct microscopy, and mostly having a particle size or diameter of between 1 and 6 µm, preferably at least 60% of the particles having a particle size or diameter between 1 and 3 µm, as determined by laser granulometry. This dry powder is suitably obtained by a method comprising the steps of separating, in the above-defined suspension of EPI-hNE protein, the crystals from the liquid phase, discarding the residual water and homogenizing the crumbly compact cake obtained.

The invention also relates to a dry powder comprising spheroid-like particles of EPI-hNE-4, at least 90% of the particles having a particle size or diameter between 0.5 and 4.0 µm, the MMAD being about 2.1 µm, as determined by laser granulometry. This MMAD value is well suited to ensure, when the powder is dispersed in a suitable propellant vehicle, a high respirable fraction and an effective penetration into the lungs. This dry powder may conveniently be obtained by a method comprising the step of spray-drying a solution of EPI-hNE protein.

The invention also concerns an inhalable pharmaceutical formulation comprising the above-defined suspension of the EPI-hNE-4 protein or a dry powder aerosol comprising the above-defined dry powder in a suitable propellant vehicle.

The invention further concerns methods for the preparation of a suspension of EPI-hNE protein, starting either from a solution of EPI-hNE protein or from a freeze-dried powder.

When starting from a solution of EPI-hNE protein, a suitable method for preparing the suspension comprises the steps of:

(a) bringing the pH of the solution to a value comprised between 3.5 and 4.5, so as to allow crystallization of the EPI-hNE protein, and (b) bringing the pH to a value between 3.0 and 8.0.

The above steps (a) and (b) can suitably be performed at a temperature from 1 to 40° C., preferably from 4 to 30° C.

When starting from a freeze-dried powder, a suitable method for preparing the suspension comprises the steps of:

(a) solubilizing the EPI-hNE protein in a buffer having a pH below 3.0

(b) bringing the pH of the solution to a value comprised between 3.5 and 4.5, so as to allow crystallization of the EPI-hNE protein, and (c) bringing the pH to a value comprised between 3.0 and 8.0.

The above steps (a), (b) and (c) can suitably be performed at a temperature from 1 to 40° C., preferably from 4 to 30° C.

The invention also concerns methods of preparing a dry powder as defined above starting from the above suspension of EPI-hNE protein, a solution or a freeze-dried powder thereof.

When starting from a suspension of EPI-hNE protein the method for preparing the dry powder comprises the steps of separating, in the above suspension, the crystals from the liquid phase, e.g. by centrifugation or filtering on a submicronic filter, discarding the residual water, suitably using a method not causing extensive compacting of the solid phase cake, e.g. by gentle evaporation at a temperature below 40° C. and a pressure slightly below atmospheric pressure, and homogenizing the solid cake obtained so as to individualize the agglomerated particles, suitably by techniques well known in the art of milling e.g. using a Pulverisette 5 (planetary mill) from Fritsch or an electric milling apparatus Moulin JK from Laboratoire Moderne, Paris.

When starting from a solution of EPI-hNE protein a suitable method for preparing the dry powder comprises the steps of (a) bringing the pH of the solution to a value comprised between 3.5 and 4.5, so as to allow crystallization of the EPI-HNE protein.

(b) separating, in the above suspension, the crystals from the liquid phase, e.g. by centrifugation or filtering on a submicronic filter, (c) discarding the residual water, suitably using a method not causing extensive compacting of the solid phase cake, preferably by gentle evaporation at a temperature below 40° C. and a pressure slightly below atmospheric pressure, (d) homogenizing the solid cake obtained so as to individualize the agglomerated particles, suitably by techniques well known in the art of milling.

The above steps (a) and (b) can suitably be performed at a temperature from 1 to 40° C., preferably from 4 to 30° C.

When starting from a solution of EPI-hNE protein a preferred method comprises the step of spray-drying this solution. The parameters of this step may conveniently be adjusted to ensure a particle size distribution such as to ensure, when the powder is dispersed in a suitable propellant vehicle, a high respirable fraction and an effective penetration into the lungs.

When starting from a freeze-dried powder of EPI-hNE protein a suitable method for preparing the dry powder comprises the steps of:

(a) solubilizing the EPI-hNE protein in a buffer having a pH below 3.0

(b) bringing the pH of the solution to a value comprised between 3.5 and 4.5, so as to allow crystallization of the EPI-hNE protein.

(c) separating, in the above suspension, the crystals from the liquid phase, preferably by centrifugation or filtering on a submicronic filter.

(d) discarding the residual water, suitably using a method not causing extensive compacting of the solid phase cake, preferably by gentle evaporation at a temperature below 40° C. and a pressure slightly below room pressure, and (e) homogenizing the solid cake obtained so as to individualize the agglomerated particles, suitably by techniques well known in the art of milling.

The above steps (a) and (b) can suitably be performed at a temperature from 1 to 40° C., preferably from 4 to 30° C.

The invention also concerns the use of the above suspension or dry powder aerosol of an EPI-hNE protein for the preparation of medicaments for treating a disease condition which is due to an excessive activity of hNE.

The disease condition may be, in particular, any respiratory disorder or may be selected from the group consisting of cystic fibrosis, emphysema, ARDS (Acute Respiratory Distress Syndrome) and COPD (Chronic Obstructive Pulmonary Disease).

The examples which follow will serve to better describe the invention, but are in no way to be considered as being limitative.

The following description will be better understood by referring to FIGS. 1 to 3B.

EXAMPLE 1

Purification of EPI-HNE4

Figure 1:
FIG. 1 is a micrograph of the pellet obtained after centrifugation of an EPI-HNE4 suspension showing the rod-like structure of the EPI-hNE-4 crystals in presence of water.

Yeast Production System.

The hNE inhibitors are produced as secreted proteins in the culture supernatants of high cell density *Pichia pastoris* strain GS115 fermentations.

Expression plasmids are constructed by ligating synthetic DNA sequences encoding the *Saccharomyces cerevisiae* mating factor α prepropeptide directly to the 5'-terminus of synthetic DNA encoding the desired hNE inhibitor. This fusion gene is sandwiched between an upstream inducible *P. pastoris* aox1 gene promoter and downstream aox1 gene transcription termination and polyadenylation sequences that are carried on a plasmid that also encodes a *S. cerevisiae* his4 gene.

Linearized expression-plasmid DNA is incorporated by homologous recombination into the genome of the *P. pastoris* strain GS115 by spheroplast transformation. Regenerated spheroplasts are selected for growth in the absence of added histidine. Individual isolates are screened for methanol utilization phenotype (mut+), secretion levels, and gene copy number. Strain PEY-53 secreting a high level of EPI-HNE-4 was thus selected. This strain is estimated by Southern analysis of genomic DNA to contain four copies of expression plasmid DNA integrated into the aox1 gene locus.

Protein Production

*P. pastoris* strain PEY-53 are grown in mixed-feed fermentations similar to the procedure described in WO 96/20278, with the difference that pressurized air is used instead of purified oxygen. Briefly, cultures are first grown in batch mode with glycerol as the carbon source. After exhaustion of glycerol, the cultures are grown for about four hours in glycerol-limited feed mode to further increase cell mass and to derepress the aox1 promoter. In the final production phase, the cultures are grown in methanol-limited feed mode. During this phase, the aox1 promoter is fully active and the hNE inhibitors are secreted into the conditioned medium (C.M.) The final concentration of EPI-hNE-4 in the PEY-53 fermentation C.M. was about 1000 mg/l as determined by SDS-PAGE analysis and by RP-HPLC. The major molecular species produced by PEY-53 cultures is the properly processed EPI-hNE-4 protein. However, this strain also secretes about 5–20% of a protein having slightly higher molecular weight presumably representing alternatively processed EPI-hNE-4 protein. The correctly processed EPI-hNE-4 can be purified substantially free of these contaminants as described below.

100 l of the PEY-53 CM obtained as described in Example 1 were collected and passed over an expanded bed as follows: 10 l of chromatographic matrix (Streamline SP from Amersham-Pharmacia) is equilibrated in 50 mM ammonium acetate pH 3.5 and fluidized in the same buffer to 30 l at 300 cm/h. After loading, the column is washed in 10 mM ammonium acetate pH 3.5 to obtain an absorption at 280 nm below 0.05. The beads are packed to 10 l and EPI-hNE-4 is recovered by washing the column in 1 M ammonium acetate pH 4.5 buffer.

Thus was obtained a 10 l solution containing about 100 g of EPI-hNE-4 (as determined by spectrometric assay at 280 nm, by RP-HPLC, Coomassie protein assay and biological activity assay).

RP-HPLC (silica column Licrosphere 100RP from Pharmacia/gradient of water +1% TFA and acetonitrile +1% TFA) showed that the alternatively processed form is not separated from the correct form. The contamination by green contaminants is also detectable.

The solution was sterile-filtered on a 22 μm filter (Millipack 200 from Millipore) before further purification.

Hydrophobic interaction chromatography was conducted by passing the above 10 l solution on a BioProcess (Pharmacia) system, using a phenyl-sepharose Fast Flow matrix from Pharmacia in a 15 l BPTG column from Pharmacia. The buffers used were A: sodium acetate 50 mM pH 4.5+1M NaCl, and B: sodium acetate 50 mM pH 4.5. The elution was performed in one step at 100% B with a flow rate was 300 cm/h.

The eluate contained about 50 g of purified EPI-hNE4 (as determined by spectrophotometric assay at 280 nm, Coomassie protein assay and biological activity assay).

RP-HPLC showed that the alternatively processed form was not separated. No green pigment was detectable.

Cation exchange chromatography was then performed using a Bioprocess chromatographic system from Pharmacia. The matrix used was Macroprep High S matrix from BioRad (rigid matrix based on cross-linked methacrylate carrying sulphonate surface groups), in a 15 l BPG200 column from Pharmacia. The buffers used were A: ammonium acetate 10 mM pH 3.5, B sodium acetate 50 mM pH 6.2 and, C: 10 mM ammonium bicarbonate pH 7.8. A first elution in buffer B was used to separate the misprocessed form. Elution was then performed by one step at 100% B with a flow rate of 300 cm/h.

The eluate contained about 40 g of purified EPI-hNE4 (as determined by spectrometric assay at 280 nm, Coomassie protein assay and biological activity assay), corresponding to an overall yield of the purification process of about 40%.

RP-HPLC showed less than 1.5% of the alternatively processed form. No green pigment was detectable.

The eluate was freeze-dried and kept at −20° C.

EXAMPLE 2

Preparation of EPI-hNE4 Formulations

Starting from the EPI-hNE4 freeze dried powder obtained in Example 1, 12 batches of the following EPI-HNE4 suspensions were prepared using the method described below.

Formulation 10/4: suspension of 10 mg/l EPI-hNE4 in sodium acetate and sodium chloride solution of pH 4.0

Formulation 10/5: suspension of 10 mg/l EPI-hNE4 in sodium acetate and sodium chloride solution of pH 5.0

Formulation 5/4: suspension of 5 mg/l EPI-hNE4 in sodium acetate and sodium chloride solution of pH 4.0

Formulation 5/5: suspension of 5 mg/l EPI-hNE4 in sodium acetate and sodium chloride solution of pH 5.0

Formulation 2.5/4: suspension of 2.5 mg/l EPI-hNE4 in sodium acetate and sodium chloride solution of pH 4.0

Formulation 2.5/5: suspension of 2.5 mg/l EPI-hNE4 in sodium acetate and sodium chloride solution of pH 5.0

Formulation 20/4 (4° C.) suspension of 20 mg/l EPI-hNE4 in sodium acetate and sodium chloride solution of pH 4.0, prepared at a temperature of 4° C.

Formulation 20/4 (30° C.) suspension of 20 mg/l EPI-hNE4 in sodium acetate and sodium chloride solution of pH 4.0, prepared at a temperature of 30° C.

Formulation 30/4 (4° C.): suspension of 30 mg/l EPI-hNE4 in sodium acetate and sodium chloride solution of pH 4.0, prepared at a temperature of 4° C.

Formulation 30/4 (30° C.): suspension of 30 mg/l EPI-HNE4 in sodium acetate and sodium chloride solution of pH 4.0, prepared at a temperature of 30° C.

Formulation 50/4 (4° C.): suspension of 50 mg/l EPI-HNE4 in sodium acetate and sodium chloride solution of pH 4.0, prepared at a temperature of 4° C.

Formulation 50/4 (30° C.) suspension of 50 mg/l EPI-hNE4 in sodium acetate and sodium chloride solution of pH 4.0, prepared at a temperature of 30° C.

General Method for the Preparation of Suspensions of Crystalline Particles EPI-hNE Proteins Preparation of Suspensions of 2.5, 5 and 10 mg/l EPI-hNE4

A 15 mg/ml solution of EPI-hNE-4, at pH 3.0, is prepared as follows: 140 mg of EPI-hNE-4 in powder form is solubilized in 7 ml of a 10 mM sodium acetate buffer pH 3.0. The pH is brought to 2.0 with 1M hydrochloric acid (HCl). After dissolution, the solution was filtered on a MediaKap 5 filter and the pH was brought to pH 3.0 using 1M sodium hydroxide (NaOH).

The protein concentration was checked by UV spectrophotometry and the solution was diluted with 10 mM sodium acetate to a concentration of 15 mg/ml.

Half volume of 10 mM sodium acetate, 2.4% sodium chloride pH12 was added to obtain a solution of 10 mg/ml EPI-hNE-4, pH 4.0. When necessary, the pH may be adjusted to 4±0.1 with 1M HCl or 1M sodium hydroxide.

The solution was transferred into a glass vessel and left to crystallize overnight at room temperature.

A sample of 50 μl was centrifuged and the pellet taken for contrast phase microscope analysis.

FIG. 1 is a micrograph of this pellet showing the rod-like structure of the EPI-hNE-4 crystals.

The suspension is homogenized, and then half-volume is transferred to another glass vessel and brought to pH 5.0 with 1M NaOH. At this point, the suspensions at pH 4.0 and 5.0 are repeatedly diluted as necessary to obtain concentrations of 5 mg/ml and 2.5 mg/ml.

Preparation of Suspensions of 20, 30 and 50 mg/l EPI-HNE4

Formulations 20/4 (4° C.), 20/4 (30° C.), 30/4 (4° C.) 30/4 (30° C.), 50/4 (4° C.) and 50/4 (30° C.) were prepared substantially as described above starting from 30, 45 and 75 mg/l solutions of EPI-hNE4 respectivey, all steps being performed either at a temperature of 4° C. or at a temperature of 30° C., the solution being left to crystallize during a period of 72 hours. No significant difference in the crystallization kinetics was observed between these two temperatures.

EXAMPLE 3

Analysis of the EPI-HNE4 Suspensions by Laser Granulometry

The granulometry of the EPI-HNE4 particles in the suspensions prepared in Example 2 was analyzed on a Coulter Multisizer II. Some of the results are set out in Table 1 below.

TABLE 1

| [EPI-HNE-4] mg/ml | pH | Percentage of particles having a particle size or diameter between 3 and 6 μm |
|---|---|---|
| 10 | 4.0 | 67.25 |
| 10 | 5.0 | 65.65 |
| 5 | 4.0 | 69.27 |
| 5 | 5.0 | 68.55 |
| 2.5 | 4.0 | 71.13 |
| 20 (4° C.) | 4.0 | 87.3 |
| 20 (30° C.) | 4.0 | 84.2 |
| 30 (4° C.) | 4.0 | 85.1 |
| 30 (30° C.) | 4.0 | 89.0 |
| 50 (4° C.) | 4.0 | 85.6 |
| 50 (30° C.) | 4.0 | 87.8 |

The above Table shows that in each of the suspensions at least 65% of the particles have a diameter between 3 and 6 μm.

EXAMPLE 4
Method for the Determination of the Biological Activity of the EPI-hNE4 Suspensions The biological activity of the EPI-hNE-4 suspension was confirmed by measuring the level of inhibition of human neutrophil elastase using a colorimetric test.

Human elastase hydrolyses the synthetic substrate N-methoxysuccinyl-ala-ala-pro-val-p-nitroanilide.

During hydrolysis, the product p-nitroanilide (yellow color) is released. The biological activity of EPI-hNE-4 is thus calculated with respect to the level of inhibition of human elastase, by following the decrease in the liberation of p-nitroanilide.

Various dilutions of a suspension of EPI-hNE-4 are prepared, noting the specific protein concentration by UV spectrophotometry using as diluting solution Tris 100 mM, NaCl 50 mM, Triton X100 0.25%, BSA 0.1%, pH 8.0. 100 $\mu$l of the diluted 100 nM EPI-hNE-4 are added to 5 ml test tubes. 100 $\mu$l of hNE 100 nM in the same buffer is added and the diluted samples are incubated for 15 minutes at room temperature (stirring is not necessary). 100 $\mu$l of 4.2 mM substrate (as described above) is added, and the mixture is incubated for 15 minutes at 37° C. the reaction is stopped by addition of 50 $\mu$l glacial acetic acid. The absorbance at 410 nm wavelength is measured, using the buffer alone and the hNE without EPI-hNE-4 sample as controls.

EXAMPLE 5
Stability of the EPI-hNE4 Suspensions

The size distribution and the inhibitory activity of EPI-hNE4 of 3 suspensions of EPI-hNE-4 concentrations 2.5, 5 and 10 mg/ml at pH 5.0 and 3 suspensions of EPI-hNE-4 concentrations 20, 30 and 50 mg/ml at pH 4.0 were analyzed over a two-month period, in order to verify their stability.

Suspensions were prepared according to the method outlined in Example 2. Three vials of each suspension were stored at room temperature for two months for the 3 suspensions of EPI-hNE4 concentrations 2.5, 5 and 10 mg/ml at pH 4.0 and at 4° C. for the 3 suspensions of EPI-hNE-4 concentrations 20, 30 and 50 mg/ml at pH 4.0.

The biological activity of the suspensions was determined at the start and at the end of the two month period using the calorimetric human neutrophil elastase inhibition assay as described in Example 4 above. No significant difference was found between the start and the end of the two-month period.

The size distribution of the particles was measured by laser granulometry using a Coulter Multisizer II at the start and finish of the two-month period. There is no significant modification in the size distribution of the suspension of EPI-HNE4 10 mg/ml, pH 5.0 after a 2 month storage period at room temperature.

The size distribution and the inhibitory activity of EPI-HNE4 of the suspension of EPI-hNE-4 concentrations 10 mg/ml at pH 5.0 did not show any significant change after 10 month storage at room temperature.

EXAMPLE 6
Nebulisation of the EPI-HNE4 Suspensions. Size Distribution Analysis and Microscopic Observation of the Nebulisate Droplets The suspensions prepared in Example 2 were nebulized in a Pari LC-star Jet Nebulizer.

The inhalable mass, determined according to procedures well known in the art, was about 40–50%, which is a good value for an inhalable pharmaceutical formulation.

The nebulisate particle size distribution was analyzed by laser granulometry on a Coulter Multisizer II. The MMAD was 3–4 $\mu$m.

The nebulisate particle size distribution was analyzed by impactor granulometry on successive filters of 8.0 $\mu$m, 6.0 $\mu$m, 4.0 $\mu$m, 3.0 $\mu$m, 2.0 $\mu$m, 1.5 $\mu$m, 1.0 $\mu$m. 0.75 $\mu$m, 0.5 $\mu$m and 0.25 $\mu$m, according to procedures well known in the art. For each of the suspensions tested, an MMAD of about 2 $\mu$m was found.

Figure 2:
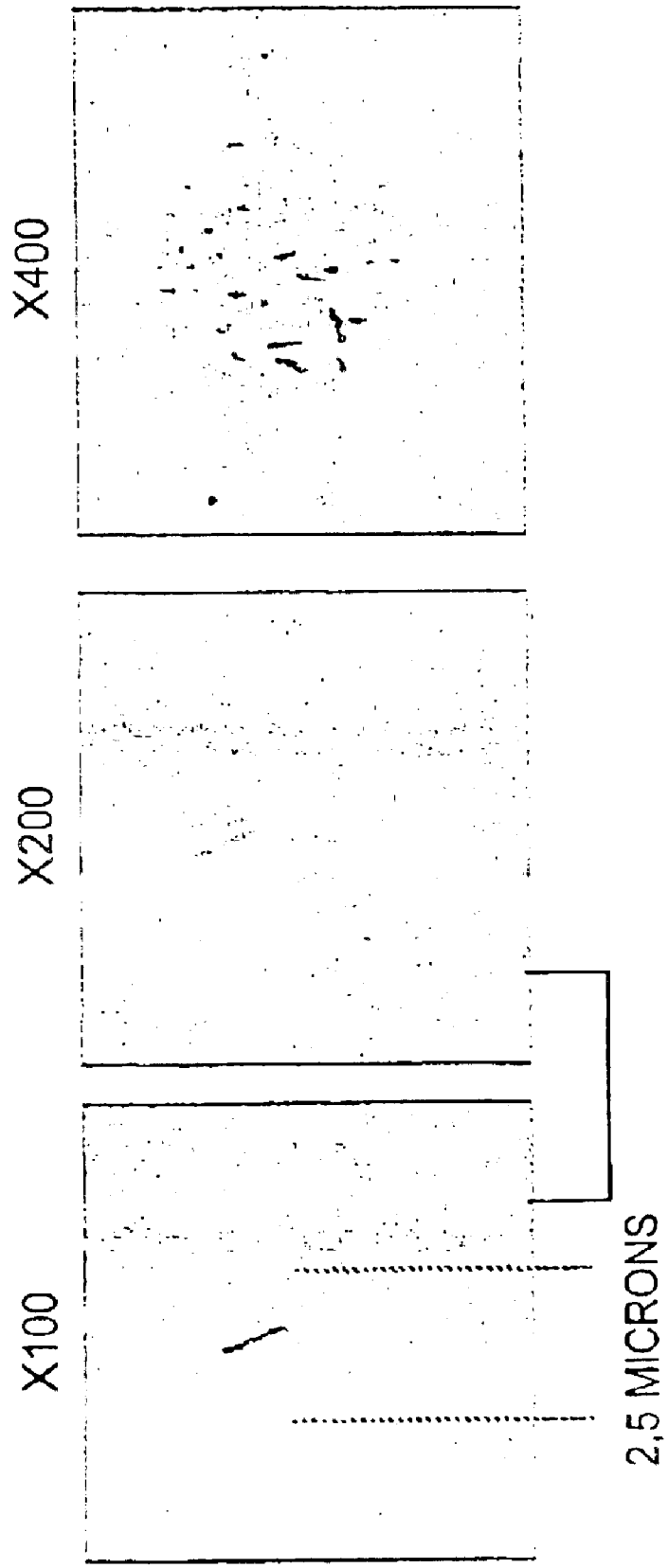
FIG. 2 is a micrograph of a nebulisate droplet having a diameter of about 2.5 μm and containing a rod-shaped EPI-HNE4 crystalline particle.

FIG. 2 is a micrograph of a nebulisate droplet having a diameter of about 2.5 $\mu$m and containing a rod-shaped EPI-hNE4 crystalline particle.

EXAMPLE 7

Preparation of a Dry Powder, Analysis of Said Powder by Microscopic Observation and Determination of its Biological Activity A 15 mg/ml solution of EPI-hNE-4, at pH 3.0, is prepared as follows: 140 mg of EPI-hNE-4 in powder form is solubilized in 7 ml of a 10 mM sodium acetate buffer pH 3.0. The pH is brought to 2.0 with 1M hydrochloric acid (HCl). After dissolution, the solution was filtered on a MediaKap 5 filter and the pH was brought to pH 3.0 using 1M sodium hydroxide (NaOH).

The protein concentration was checked by UV spectrophotometry and the solution was diluted with 10 mM sodium acetate to a concentration of 15 mg/ml.

Half volume of 10 mM sodium acetate, 2.4% sodium chloride pH 12 was added to obtain a solution of 10 mg/ml EPI-hNE-4, pH 4.0. When necessary, the pH may be adjusted to 4±0.1 with 1M HCl or 1M sodium hydroxide.

The solution was transferred into a glass vessel and left to crystallize during 72 hours at room temperature.

The suspension was filtered on a 0.22 $\mu$m filter. The filter was recovered and dried overnight in a dessicator containing blue silica gel (system allowing gradual evaporation of water). A crumbly compact powder was recovered from the filter. Simple manual mechanical homogenization was performed using a mortar, thereby yielding a very fine visually homogeneous powder.

Figure 3A:
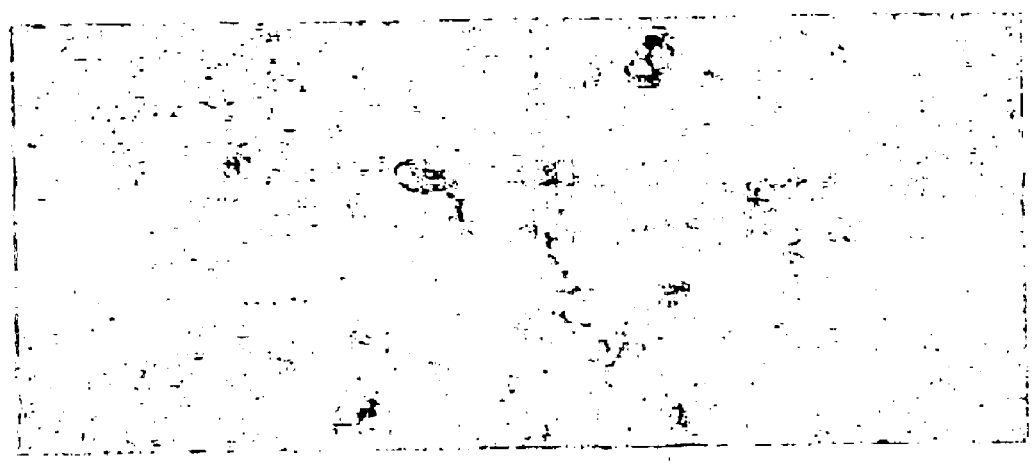
FIGS. 3A and 3B are micrographs of the dry powder showing the spheroid-like structure of the EPI-hNE4 particles in dry form.

This powder was observed by direct microscopy on a Thomas plate. FIG. 3A is a micrograph of the powder showing the irregular spheroid-like structure of EPI-HNE4 in dry form, most of the individual particles having a diameter or particle size between 1 and 6 $\mu$m.

The dark zones in the micrograph probably represent superposition of individual particles or remaining agglomerates of the manually insufficiently homogenized sample.

Statistical analysis of the diameter of the individual particles (mean of the largest and the smallest diameter of the spheroid-like particles) measured on direct microscopy Thomas plate micrographs showed that most (over 80%) of the particles have a diameter (or particle size) between 1 and 6 $\mu$m, at least 75% of the particles having a diameter (or particle size) between 1 and 3 $\mu$m. The median diameter (or particle size) is about 2.1 $\mu$m and the mean diameter (or particle size) is 2.33±0.18 $\mu$m.

The powder was dispersed in a 1% NaCl solution and analyzed by laser granulometry on a Coulter Multisizer II. The complete statistical analysis of the laser granulometry data showed a particle size distribution very similar to that obtained in Example 3, at least 65% of the particles having a diameter (or particle size) between 1 and 6 $\mu$m.

A suspension of 10 mg/ml of EPI-hNE4 at pH 5.0 was prepared from this powder by a procedure very similar to that described in Example 2. The biological activity of the suspension was determined using the calorimetric human neutrophil elastase inhibition assay as described in Example 4 above. This biological activity was not significantly different from that determined for the suspension of 10 mg/ml of EPI-hNE4 at pH 5.0 in Example 5.

EXAMPLE 8
Preparation of a Dry Powder and Analysis thereof by Laser Granulometry A dry powder was prepared from 2 l of suspension obtained during the production of previous batches of EPI-hNE-4.

The suspension was centrifuged 30 min at 10000 g. The supernatant was discarded and the resulting pellet was homogenized in 100 ml of 10 mM ammonium bicarbonate buffer. The suspension was filtered on a 0.22 $\mu$m filter. The filter was recovered and dried overnight in a dessicator containing blue silica gel (system allowing gradual evaporation of water). Four g of a crumbly compact powder was recovered from the filter. Homogenization was performed using an electric milling apparatus Moulin JK from Laboratoire Moderne, Paris, thereby yielding a very fine visually homogeneous powder.

The granulometry of this powder was analyzed on a Malvern apparatus (Malvern Mastersizer 2000 (Malvern, UK), equipped with a dry sampler <<Stirocco 2000>>.).

The results showed that most of the particles (over 80%) have a diameter (or particle size) between 1 and 6 $\mu$m, at least 60% of the particles having a diameter (or particle size) between 1 and 3 $\mu$m. The median diameter (or particle size) was about 2.66 $\mu$m.

EXAMPLE 9
Preparation of a Dry Powder by Spray-Drying and Analysis thereof by Laser Granulometry and Biological Assay 1 g of EPI-hNE4 in powder form or in crystallized form (see Example 8) was solubilized in water containing 1% hydrochloric acid pH 2.5. This solution was spray-dried (atomized) using a mini-spray drier Buchi B191.A under the conditions below:

internal diameter of the spayer: 0.7 mm spaying flow rate: 3.4 g/l air pressure: 600 l/h drying air flow rate: 35 m³/h drying air inlet temperature: 120° C.

drying air outlet temperature: 74–75° C.

Figure 3B:

The powder was observed by direct microscopy on a Thomas plate. FIG. 3B is a micrograph of the powder showing the irregular spheroid-like structure of EPI-HNE4 in dry form, most of the individual particles having a diameter or particle size between 1 and 3 $\mu$m. The absence of dark zones compared to FIG. 3A shows the good homogeneity of the powder.

The size distribution of the powder particles was analyzed by laser granulometry using a Malverne Multisizer 2000 equipped with a dry sampler Scirocco 2000.

The results showed that 90% of the particles have a diameter or particle size 0.5–4.0 $\mu$m, 75% a diameter or particle size 0.5–2.8 $\mu$m, 60% a diameter or particle size 0.5–2.2 $\mu$m, the MMAD being 2.16 $\mu$m.

Determination of the specific biological activity of the powder, as described in Example 4, showed that the protein was fully active.

What is claimed is:

1. A suspension of an EPI-hNE protein, wherein the EPI-hNE protein is present in the form of crystalline particles mostly having a diameter or particle size comprised between 1 and 6 $\mu$m, as determined by laser granulometry, the concentration of the suspension in EPI-hNE being comprised between 1 and 80 mg/ml, in an aqueous vehicle at a pH comprised between 3 and 8.

2. Suspension according to claim 1, wherein the EPI-hNE protein is present in the form of crystalline particles mostly having a diameter or particle size comprised between 3 and 6 $\mu$m, as determined by laser granulometry.

3. Suspension according to claim 1, wherein the concentration of the suspension in EPI-hNE is comprised between 2 and 50 mg/ml.

4. Suspension according to claim 1, wherein said pH is comprised between 4 and 6.

5. Suspension according to claim 1, wherein said pH is comprised between 4 and 5.

6. Suspension according to claim 1, wherein the aqueous vehicle is a saline solution having an iso-osmotic pressure.

7. Suspension according to claim 1, wherein the saline solution comprises sodium acetate and sodium chloride or sodium citrate.

8. Suspension according to claim 1, wherein the EPI-hNE protein is EPI-hNE4.

9. Suspension according to claim 8, wherein at least 65% of the crystalline particles of EPI-hNE-4 have a particle size or diameter of between 3 and 6 $\mu$m, as determined by laser granulometry.

10. Suspension according to claim 1, in the form of nebulisate droplets containing EPI-HNE4 crystallized particles which have an MMAD of about 2 $\mu$m, as determined by impactor granulometry.

11. Dry powder comprising spheroid-like particles of EPI-hNE-4 mostly having a diameter or particle size between 1 and 6 $\mu$m, as determined by direct microscopy.

12. Dry powder comprising spheroid-like particles of EPI-hNE-4, wherein at least 75% of the particles have a diameter or particle size between 1 and 3 $\mu$m, as determined by direct microscopy.

13. Dry powder comprising spheroid-like particles of EPI-hNE-4 mostly having a diameter or particle size between 1 and 6 $\mu$m, as determined by laser granulometry.

14. Dry powder comprising spheroid-like particles of EPI-hNE-4, wherein at least 60% of the particles have a diameter or particle size between 1 and 3 $\mu$m, as determined by laser granulometry.

15. Dry powder comprising spheroid-like particles of EPI-hNE-4, at least 90% of the particles having a diameter or particle size between 0.5 and 4.0 $\mu$m, the NMAD being about 2.1 $\mu$m, as determined by laser granulometry.

16. Inhalable pharmaceutical formulation comprising a suspension or a dry powder according any one of claims 1–15 in a suitable propellant vehicle.

17. Method for preparing a suspension of an EPI-hNE protein according to claim 1, comprising, starting from a solution containing an EPI-hNE protein, the steps of (a) bringing the pH of the solution to a value comprised between 3.5 and 4.5, so as to allow crystallization of the EPI-hNE protein, and (b) bringing the pH to a value between 3.0 and 8.0.

18. Method for preparing a suspension of an EPI-hNE protein according to claim 1, comprising, starting from a freeze dried powder of an EPI-hNE protein, the steps of (a) solubilizing the EPI-hNE protein in a buffer having a pH below 3.0

(b) bringing the pH of the solution to a value comprised between 3.5 and 4.5, so as to allow crystallization of the EPI-hNE protein, and (c) bringing the pH to a value comprised between 3.0 and 8.0.

19. Method of preparing a dry powder comprising spheroid-like particles of EPI-hNE-4 mostly having a diameter or particle size between 1 and 6 μm comprising the steps of separating, in a suspension according to claims 1–10, the crystals from the liquid phase, discarding the residual water and homogenizing the crumbly compact cake obtained.

20. Method of preparing a dry powder according to claim 19 comprising the step of spray-drying a solution of the EPI-hNE protein.

21. Method for treating a disease condition which is due to an excessive activity of hNE comprising the step of administering an inhalable pharmaceutical formulation according to claim 16 to a subject in need thereof.

22. Method according to claim 21 wherein the condition is a respiratory disorder or is selected from cystic fibrosis, emphysema, ARDS (Acute Respiratory Distress Syndrome) and COPD (Chronic Obstructive Pulmonary Disease).

\* \* \* \* \*